United States Patent
Banta et al.

(10) Patent No.: US 8,015,031 B2
(45) Date of Patent: Sep. 6, 2011

(54) METHOD AND COMPUTER READABLE MEDIUM FOR MERGING STUDIES

(75) Inventors: Christina Banta, Andover, MA (US); Sheila Filteau, Methuen, MA (US); Brian Collamore, Rutland, MA (US); Joseph M. Luszcz, Hudson, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 3121 days.

(21) Appl. No.: 09/876,782

(22) Filed: Jun. 7, 2001

(65) Prior Publication Data
US 2002/0188475 A1   Dec. 12, 2002

(51) Int. Cl.
*G06F 19/00* (2006.01)
(52) U.S. Cl. ........... 705/3; 705/2; 709/219; 600/300; 600/425
(58) Field of Classification Search .......... 705/2, 3; 714/48; 707/8, 104.1; 715/523; 600/425; 709/219
See application file for complete search history.

(56) References Cited

U.S. PATENT DOCUMENTS

| | | | | |
|---|---|---|---|---|
| 5,546,580 A | * | 8/1996 | Seliger et al. | 707/8 |
| 5,605,153 A | * | 2/1997 | Fujioka et al. | 600/425 |
| 5,671,353 A | * | 9/1997 | Tian et al. | 714/48 |
| 5,675,744 A | * | 10/1997 | Tsujii | 705/3 |
| 5,676,744 A | * | 10/1997 | Thakkar et al. | 106/31.86 |
| 5,713,350 A | * | 2/1998 | Yokota et al. | 705/3 |
| 5,915,242 A | * | 6/1999 | Tsujii | 705/3 |
| 6,574,629 B1 | * | 6/2003 | Cooke et al. | 707/10 |
| 6,611,846 B1 | * | 8/2003 | Stoodley | 707/104.1 |
| 2002/0016718 A1 | * | 2/2002 | Rothschild et al. | 705/2 |
| 2002/0143824 A1 | * | 10/2002 | Lee et al. | 707/523 |

FOREIGN PATENT DOCUMENTS

| | | |
|---|---|---|
| WO | WO0014652 | 3/2000 |
| WO | WO0065522 | 11/2000 |

OTHER PUBLICATIONS

Digital Imaging and Communications in Medicine (DICOM) Part 5: Data Structures and Encoding, National Electrical Manufacturers Association, Rosslyn, VA 22209 (USA), 2000.

* cited by examiner

*Primary Examiner* — Dilek B Cobanoglu

(57) ABSTRACT

A method and a computer readable medium for merging two or more separate unique studies based upon context-specific content, and merging the two or more separate studies, each with a unique identifier, into a composite study containing artifacts of the two or more merged studies, with the composite study having a single unique identifier.

28 Claims, 3 Drawing Sheets

METHOD AND COMPUTER READABLE MEDIUM FOR MERGING STUDIES

BACKGROUND OF THE INVENTION

1. Field of the Invention

The present invention relates to a method and computer readable medium for merging studies. More particularly, the present invention relates to a method and computer readable medium for merging medical studies into a composite medical study in a medical information management system.

2. Description of the Related Art

Typically, a physician will order or prescribe for a patient certain examinations, such as an X-ray or ultrasound examination. When such an examination is being performed, a user will typically generate a "medical" study which will contain the examination results. The study may be stored according to a DICOM (Digital Imaging and Communication in Medicine) standard, a format for Agilent Technology's medical information management system called EnConcert, known as DSR-TIFF, or as another storage format. DICOM is a prevailing standard for medical imaging management, with EnConcert conforming thereto. According to DICOM lexicon, when an examination is to be performed, a "Requested Procedure" is generated, where collected information will be collated. Likewise, according to DICOM, the term "study" corresponds to a collection of information associated with the Requested Procedure, i.e., the collection of information associated with the examination being performed. Likewise, the term "study" in EnConcert, similarly relates to DICOM's information collection that is associated with the Requested Procedure. In embodiments of applicants' invention, the term "study" corresponds to the "collected," rather than "collecting of," information for an examination, and most closely relates to an overall combination of "Performed Procedure Steps," according to the DICOM standard, with each DICOM Performed Procedure Step including the collected information. In the embodiments of applicants' invention, the term "procedure" will be used to correspond to a similar combination of collected information, as in the DICOM Performed Procedure Step, with a study having potentially multiple procedures. Lastly, in the embodiments of applicant's invention, the term "protocol" corresponds to an identification of a type of examination, e.g., a stress test, including either standard or individualized instructions as to what data is to be, or was, collected for such an examination, or even how the collected data is to be collated or calculated.

A problem surfaces when the user performs a multiple number of save attempts or transmissions, during an examination, either intentionally or by accident. Some examples of this scenario include: 1) an inadvertent termination of the examination while in progress, due to user error; 2) deliberate premature termination of the examination, either to accommodate the patient's or another patient's needs; 3) a request for additional artifacts, including, but not limited to, images and/or measurements based on a preliminary review of a study including the information obtained in the examination; or 4) failing of transmissions, thereby fragmenting information related to a single examination into more than one study upon an attempted re-transmission, though this fragmenting of information is less prevalent in more robust systems. The multiple save attempts or transmissions can cause separate studies to be created, where the separate studies should logically be considered as corresponding to one examination or related examinations. Each study generated may have its own unique identifiers (UIDs), which may cause errors or difficulty in generating a single diagnostic report based on the different studies.

Conventionally, to prevent these above problems, some systems have been designed to collate all the information for an examination before sending the information to a medical information management system, where the collated information is included in one study. According to this technique, when a physician requests an examination to be performed, a Study Instance UID is allocated to the Requested Procedure. Typically, using a DICOM Modality Worklist service or other schemes, a list of Requested Procedures may be accessed on acquisition equipment, with one Requested Procedure being selected for a particular patient examination. This permits the acquisition equipment to mark every deliverable artifact of the examination, e.g., images, measurements, and reports, etc, with the Study Instance UID before sending the artifacts, to the medical information management system, viewer, or archive. Thus, the receiving equipment may unambiguously identify all artifacts related to the original study. Subsequent examinations may be performed and information acquired from the same Requested Procedure, which would also have all deliverable artifacts marked with the same Study Instance UID. As long as both acquisition equipment and receiving equipment are implemented in an intended manner, the need of merging two associated studies would be reduced, as the generation of multiple studies, corresponding to multiple Requested Procedures with different Study Instance UIDs, is typically prevented.

However, if the subsequent examinations are not performed using the acquisition equipment with the proper Requested Procedure, having the proper Study Instance UID, a different study may be generated in the receiving equipment and the new collected artifacts would not be combined with the proper study. Also, additional studies may be generated if the examination is performed in an emergency room situation, without a study order or manual entry of patient identification to acquire the Requested Procedure, or perhaps while a network is down. Further, additional studies may be generated when a related examination is performed by different health providers with differing systems, and thus be based on a different Requested Procedure or perhaps not even based on a Requested Procedure. These examples are only illustrative of the problems associated with the conventional systems and should not be considered as being limiting of the potential problems not listed herein.

Therefore, to overcome these problems associated with the generation of two or more logically related separate studies, the present invention sets forth a merging capability for the separate unique studies.

SUMMARY OF THE INVENTION

An embodiment of the present invention is directed to merging two or more separate unique studies into a composite study.

In another embodiment of the present invention two DICOM studies are merged by adding the medical information of the first study to a second study, reconciling the identifiers within the second study, and deleting a distinct database identity of the first study. Additionally, according to an embodiment of the present invention, the merged studies do not have to conform to a DICOM standard to be merged.

A further embodiment of the present invention sets forth a merging method, including merging a patient's first medical study with a logically related second medical study, such that the resultant composite study is the first medical study and has a study identifier of the first medical study, wherein the merging includes an automatic adding of medical information of the second medical study to the first medical study.

An additional embodiment of the present invention sets forth a study merging method, including merging a patient's first medical study with a logically related second medical study, such that medically context-specific information stored in at least one of the first and second medical studies is merged based upon a protocol of at least one of the first and second studies, the protocol being indicated by an attribute of at least one of the first and second studies.

An additional embodiment of the present invention sets forth a computer readable medium having a program to control a computer to merge a patient's first medical study with a logically related second medical study, such that the resultant composite study is the first medical study and has a study identifier of the first medical study, wherein the merging includes an automatic adding of medical information of the second medical study to the first medical study An additional embodiment of the present invention sets forth a computer readable medium having a program to control a computer to merge a patient's first medical study with a logically related second medical study, such that medically context-specific information stored in at least one of the first and second medical studies is merged based upon a protocol of at least one of the first and second studies, the protocol being indicated by an attribute of at least one of the first and second studies.

An embodiment of the present invention is further directed to a medical study merging method, including identifying a patient's related first and second medical studies to be merged and merging the first medical study with the second medical study, such that a resultant composite medical study has a study identifier different from at least one of the first and second medical studies, wherein the merging includes an automatic adding of a series of the second medical study to the composite study, the series of the second medical study having a series identifier the same as a pre-merge corresponding series identifier, with the series of the second medical study series including at least an artifact with an artifact identifier the same as a pre-merge corresponding artifact identifier, such that the composite study includes series and corresponding series identifiers from both the pre-merged first and second medical studies.

The above embodiments and advantages of the present invention can be achieved by allowing a user to list all studies for a particular patient, select a study from the list, indicate which study the selected study is to be merged with, and then confirm the merging process. The merging of the studies is thereafter automatically performed.

BRIEF DESCRIPTION OF THE DRAWINGS

Advantages of the invention will become apparent and more readily appreciated for the following description of the preferred embodiments, taken in conjunction with the accompanying drawings of which.

DETAILED DESCRIPTION

Figure 1:
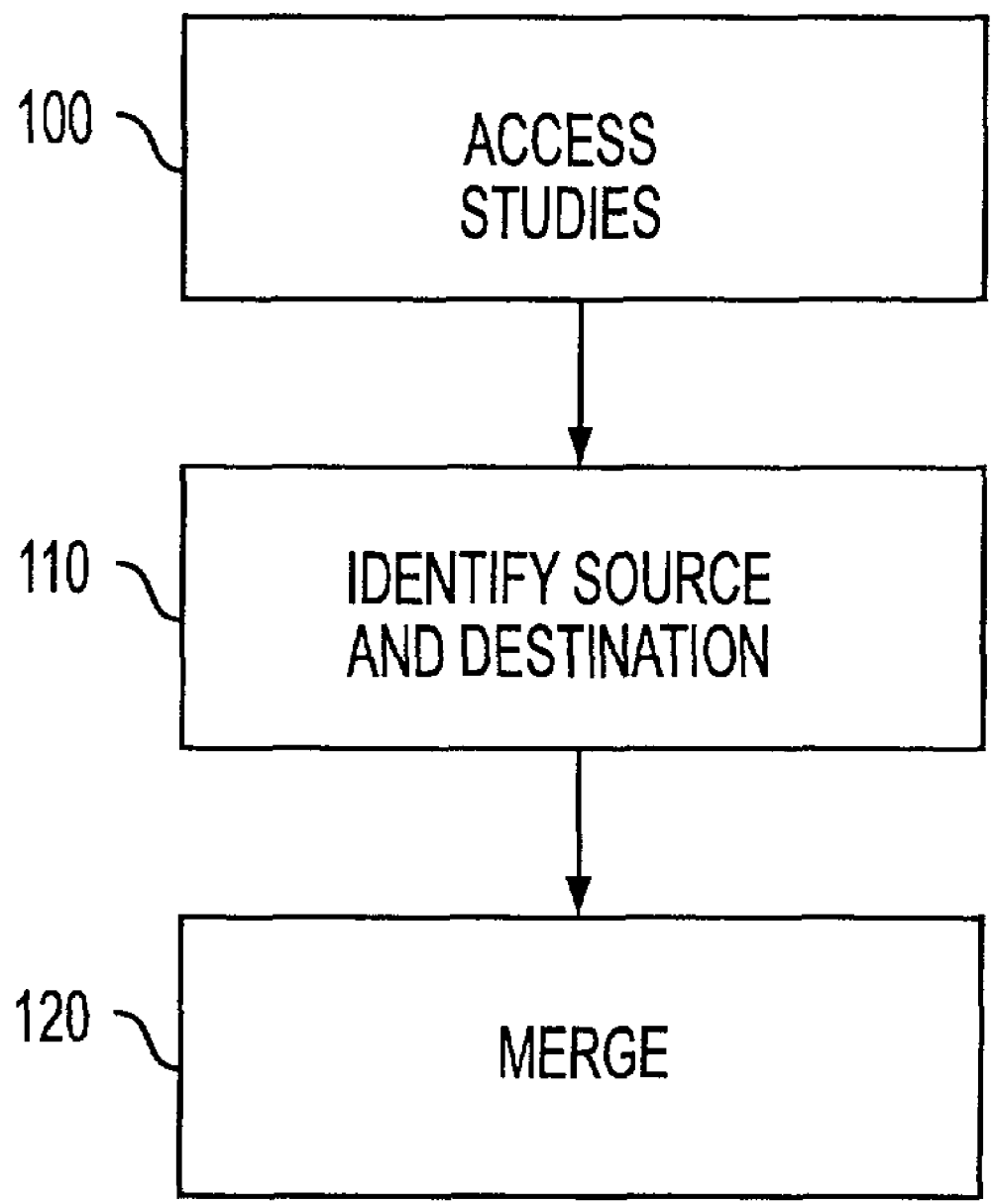
FIG. 1 is a flow chart illustrating the steps of the present merging method.

Reference will now be made in detail to the preferred embodiments, examples of which are illustrated in the accompanying drawings. In accordance with the preferred embodiments, there is provided a method and computer readable medium for merging separate unique studies.

Applicants have developed a standardized approach to healthcare medical information management that is believed to be a more accurate model of the real-world clinical environment.

Typically, when a referring physician places an order for one or more requested examinations, each of the requested examinations corresponds to a Requested Procedure and is assigned a "Requested Procedure ID." A performed examination is collected in a study corresponding to the Requested Procedure and identified by a globally unique identifier, the Study Instance UID. Additional procedures may be acquired until the examination requested in the physician's order is completed. In addition, each study may include examination information in at least one procedure, similar to DICOM's Performed Procedure Step, for example. Thus, a problem with conventional systems is that multiple generated studies could each have procedures therein which are logically related to the same examination. Usually, all logically related examinations are performed at a single location, such that a user may intuitively link two different studies identified by two different Study Instance UIDs by a Patient ID, thus intuitively alleviating this multiple study problem. However, when examinations are performed at different locations with differing systems, the Patient IDs will probably not match, thus resulting in no logical intuitive way to link the related studies.

The Study Instance UID is usually a 64 character string, with portions storing codes that are uniquely different for each vendor of medical information management systems. The remaining portions of the character string may be used to identify a single division within a vendor, and additional information related to the individual performed study. A standards agency usually assigns the vendor specific codes. Although, this description of the Study Instance UID has been set forth, every vendor typically is free to construct the UID in any manner consistent with the DICOM standard. Likewise, as the present invention may be applied in an environment applying a standard other than DICOM, the corresponding identifier may be constructed differently.

Further, as an examination is performed by an acquisition device, artifacts are generated, including but not limited to, DICOM SOP (Service Object Pair) Instances (object oriented: images, structured reporting objects, findings, comments, waveforms, Doppler audio, etc.) Each SOP instance is identified through the globally unique identifier, SOP Instance UID. The SOP instances, within a procedure of a study, produced during an examination are organized into one or more DICOM "series," each identified through a globally unique identifier, Series Instance UID. Thus, each study having a separate Study Instance UID may have multiple procedures each having a number of series, each series having a Series Instance UID, and each series potentially including a number of SOP Instance UIDs.

In a some DICOM systems, the use of Series Instance UIDs and SOP Instance UIDs are used in combination with a Series Number and an Image Number. Each series may include Series Numbers, with each Series Number having a different number, e.g., 10, 20, 30, 40 and 50. Likewise, each series may have a number of images, each represented by an Image Number. Some systems utilize these Series and Image numbers in their display systems, for example, to list series and images in a list for selection and display by a user.

In applicants' developed merging method, with each Study Instance UID being unique, merging will be performed on studies with different Study Instance UIDs. For example, merging two DICOM studies into a composite study will create an association between the two Study Instance UIDs. By allowing more than one Study Instance UID to be associated with a study, any subsequent acquisition of SOP instances identified by either of the Study Instance UIDs, may be combined with the composite study. For example, artifacts belonging to the same series (i.e., with the same Series Instance UID) as previously acquired artifacts, are acquired into the same series in the composite study as had existed in the study prior to the merging. Likewise, series and images in some DICOM systems would be merged into a series with a Series Instance ID, with the images being placed in that series, thus negating the need of the Series and Image Numbers. In applying the present merging technique, the following rules should be utilized.

1) Both studies to be merged should be directed to the same patient; and

2) Only one of the source study and a destination study should have a report. Although this is not a necessity, it is best for the healthcare of the patient to not have potentially diverging reports merged in a single study. In addition, such combination of reports usually requires human intervention to evaluate and reconcile the differences between the reports. Though, potentially multiple reports could be stored in the same study or reconciled into a single report.

In the EnConcert system, if a study has been given the status of "Final," then the status of the new composite study becomes "Reconsider." Typically, once a physician reviews a report and signs off on it, the report is given the status indicator of "Final." When there are additional exams or studies to review or the report is not complete, then the physician would have to again review the exams, studies, or report, thus these studies have been given the status indicator of "Reconsider." These status indicators are only discussed for illustrative purposes, as other systems other than EnConcert may utilize additional or different indicators to show how far along a reviewing process a study has progressed, i.e., whether the examination has just been performed or whether the physician has signed off on the study, for example.

As noted above, since each study has its own individual Study Instance UID, it is important to know which UID of the source and destination studies will be used as the composite study's Study Instance UID, for query or export operations for example. Therefore, the destination study's Study Instance UID should be considered the primary Study Instance UID, and will appear as the only Study Instance UID upon exporting or transmitting artifacts, e.g., images and structured reports. However, the source study's Study Instance UID may thereafter be used in associating newly acquired artifacts with the corresponding contents of the source study. Alternatively, the source study's Study Instance UID may be used as the primary Study Instance UID, or a Study Instance UID different from both the source and destination studies, including a newly-synthesized UID, may be used.

The Series Instance UIDs for each series of the source study should continue to be used for each corresponding series in the composite study, with the potential Series Numbers in both the source and destination series being retained but nulled, as such identifies are no longer needed. Alternatively, the Series Numbers may be retained, without nulling their values. SOP Instance UIDs for artifacts of the source study also should continue to be used for those artifacts in the composite study.

FIG. 1 is a flow chart illustrating the process of the present merging method. First, in operation 100, a user operating a medical information management system will access a listing of multiple studies for a particular patient or particular examination, i.e., logically related studies. Alternatively, systems other than the medical information management system could implement embodiments of the present invention. Preferably, a user will view the study list on a monitor of the medical information management system. The monitor could even be a PC at a users desk connecting with the medical information management system through the Internet or an internal LAN, for example. In operation 110, as the user views a listing of the studies, the user will indicate a particular study as being the source study, and a particular study as being the destination study. Preferably, using a terminal, the user will "drag" the viewed source study listing on the terminal monitor and "drop" the source study listing into the viewed destination study listing. Of course, additional methods could be implemented for such an indication of both the source and destination studies. Thereafter, in operation 120, the user confirms the merging of the selected source and destination studies.

According to this technique illustrated in FIG. 1, the merging of the source study into the destination study, to form the composite study, will be implemented.

Figure 2:
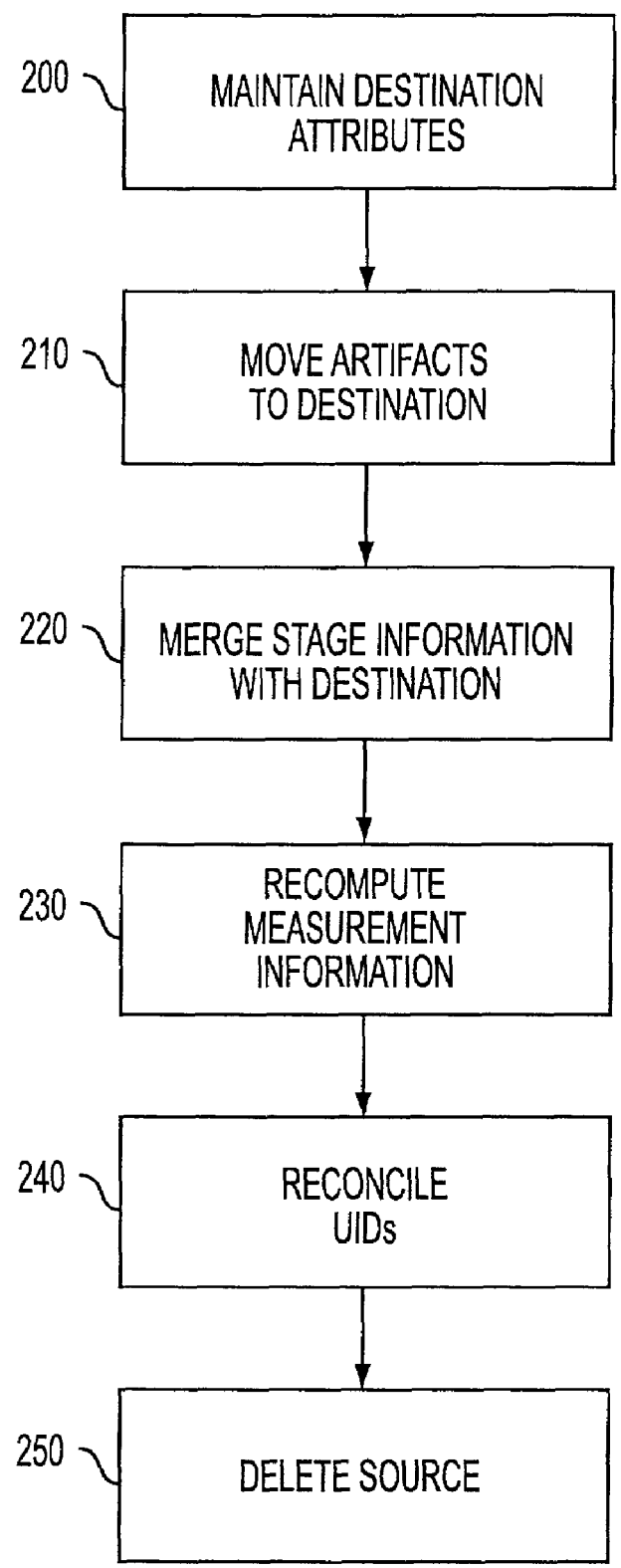
FIG. 2 is a flow chart illustrating the merging of the source study with the destination study.

FIG. 2 is a flow chart illustrating the process of merging the source study with the destination study. First, in operation 200, the attributes of the destination study are maintained. Similar to the above EnConcert status discussions, in EnConcert, if attributes of the destination study indicate that the study's status is that of "Unread" or "Preliminary," those attributes will be retained. In EnConcert, the "Unread" status indicator is indicative of a study only having been received in the medical information management system, without additional attributes being added thereto. The "Preliminary" status indicator is indicative of whether a study has had attributes added thereto, such as a technician adding measurement information, or even the study being opened after generation and then saved again, which generates an attribute due to that saving operation. Typically, a study with a "Preliminary" status indicator has not been reviewed by a physician.

In operation 210, the artifacts, if any, from the source study are then moved from the source study into the destination study. Likewise, in operations 220 and 230, context-specific algorithms are applied to the source and destination studies to determine whether context-specific information is stored therein, and whether certain algorithms should be applied during the merging of the context-specific information into the destination study, to form the composite study. Typically, the source and destination studies include protocol attributes that will indicate to the medical information management system the contents of the study and the type of study, e.g. whether the study includes stage information or measurement information, for example, noting that the present invention is not limited thereto.

As noted, one example of context-specific information would be information in either of the source or destination studies indicative of stage information. An example of stage information would be a staged stress test, where vitals of a patient will typically be measured at different stages, or time intervals, of the stress test. Each stage, or time slice, will typically be stored, e.g., the vitals of the patient may be stored at time 1 (baseline before stressing), time 2 (during stress), and at time 3 (during rest). The study will typically include protocol attribute information indicating that the study includes stage information, as well as the type of stage protocols, e.g., the aforementioned stress test. The medical information management system will accordingly apply an appropriate stage algorithm to the stage information of the source and destination studies, if applicable, thus merging stage information from the source study with stage information in the destination study. The medical information management system can determine from the protocol attributes of the source and destination studies, as well as stage protocol information available to the medical information management system, specifically how to organize and store the corresponding stage information in the destination study.

The merging of stage information from source and destination studies is independent of the type of standard the studies are stored under, i.e. it is not material to the medical information management system whether the source and destination studies are stored under the DICOM standard. The medical information management system merely utilizes the protocol attribute information of the source and destination studies to merge the stage information stored therein.

As also noted above, the source and destination studies may individually include measurement information, which may include information illustrative of the width of a heart wall, for example. The measurement information from the source study may also be merged with the destination study, as illustrated in operation 230. Similarly to the above stage merging algorithms, when measurement information is present in either of the source or destination studies then protocol attributes of the corresponding study indicate what type of examination the measurement information corresponds to, as well as how the measurement information is to be collated or calculated. For example, in measuring the width of the heart wall, a technician may have measured the width several times at different points in time. Additionally, the measurements may be indicative of measurements of different objects either at the same time or different times, for example. There are multiple examples of different types of measurement information, and the present invention is not limited only to the ones set forth herein.

Based on the protocol the measurements correspond to, different types of algorithms may be applied to the measurement information. For example, the attributes of the source study, as well as the corresponding protocol, may indicate that an averaging of all or some of the measurement information is necessary. Thus, when the source study is merged with the destination study, having a similar protocol indication, the merged measurement information will all be averaged, for example. Alternatively, based on the measurement information protocols, studies of different protocols may also be merged. The measurement protocol could, for example, require a different type of calculation to be generated using the measurement information of the separate studies upon merging. The corresponding protocol could also require that a maximum or minimum be calculated, which would probably change when source and destination studies are merged.

Alternatively, attributes of either of the source or destination studies could indicate to overrule the applicable standard protocol calculations, and use only a specific measurement or a different calculation. This could happen when a physician determines that one specific measurement is very important or is more illustrative of the overall condition of the patient, for example. These limited examples are merely for illustrative purposes, and the present invention should not be limited thereto.

Thus, if there is measurement information and, potentially, derived calculations in the destination study, then as shown in operation 230, the newly added measurement information of the source study will be merged with the measurement information of the destination study, with measurements and derived calculations in the destination study being recomputed to reflect the newly added information in accordance with the protocols corresponding to different measurement information for each study.

Similar to the merging of stage information, the merging of measurement information from source and destination studies is independent of the type of standard the studies are stored under, i.e. it is not material to the medical information management system whether the source and destination studies are stored under the DICOM standard, any standard may be used. The medical information management system merely utilizes its available measurement protocol information and the attribute information of the source and destination studies to merge the measurement information stored therein.

Although, only stage information and measurement information merging has been set forth herein, the present invention is not limited thereto. Rather, these examples are merely illustrative of the ability of the present invention to determine what type of information is stored in a study, and properly merge the information from the source study with information from the destination study, in accordance with the detected protocols, i.e. applying context-specific algorithms to the source and destination studies to provide a composite study. As noted above, these context-specific algorithms operate independently of whether a study is stored according a DICOM standard, or any other standard.

In operation 240, UIDs that uniquely identify the studies and SOP objects, if available, for exchange via the DICOM standard are reconciled, such that the composite study has a single identifying Study Instance UID, while retaining information relating to the separate UIDs of the source study, series, and artifacts, so that any incoming information related to the original source study is identified with, and properly appended to, the new composite study. It is also noted that, the single identifying Study Instance UID may be a Study Instance UID different from both the source study and the destination study or may be one of the source study and destination study's Study Instance UID, as set forth in the present embodiment.

Thereafter, in operation 250, with all the necessary information being transferred from the source study to the destination study, the distinct database identity of the source study may now be deleted. Alternatively, a new study may be generated with a new Study Instance UID, and the source and destination studies could be merged into the new study and the corresponding UIDs would thus be reconciled with the new study's UIDs, similar to the above reconciling of source UIDs within the merger of the source study into the destination study to form the composite study.

Further, authority to perform such a merging may be restricted in use to certain users, to prevent unauthorized or unintended merging of studies which are not logically related.

As noted above, new incoming information, related to an original source or destination study, may be merged with the composite study, as the composite study stores the Study Instance UIDs of the original source study, destination study, or any additional study previously merged therewith. Such information should have the source or destination study's Study Instance UID and indicate one or more Series Instance UIDs. Using such information, the corresponding new information may be merged with the composite study and placed in the appropriate series, if necessary. Likewise, the Study Instance UID of the new information may also be reconciled with the Study Instance UID of the composite study, while retaining the new information Study Instance UID and the original and destination Study Instance UIDs, as well as the corresponding Series Instance UIDs. A physician may be notified upon receipt of such new incoming information, to allow for additional review of the study.

Embodiments of the present invention may be implemented in applicants' medical information management system or with other systems which use similar identifiers. The merging method may also be utilized in systems which utilize study information with different identifiers, noting that because DSR-TIFF studies, for example, do not have the corresponding identifiers, identifiers could be synthesized therefor, before merging. Lastly, the merging set forth in the present invention may further be utilized in systems which do not utilize study identifiers similar to the UIDs set forth in the DICOM standard.

Figure 3:
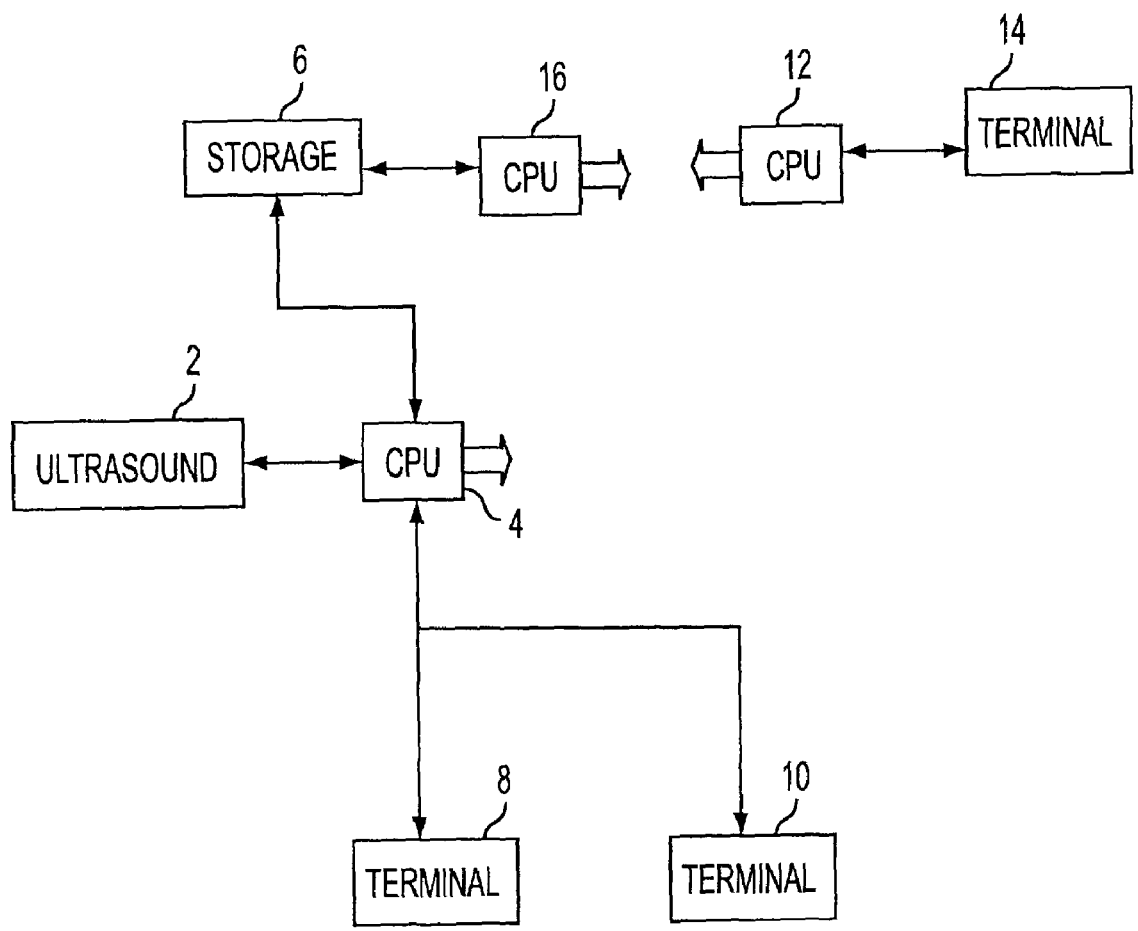
FIG. 3 is a diagram illustrating an implementation of applicants' medical information management system.

FIG. 3 illustrates a diagram of an implementation of applicant's merging method and computer readable medium. In the system of FIG. 3, a user may, for example, initiate the generation of a first study at terminal 8. CPU 4 would thus receive artifact information, for example, from Ultrasound system 2 or other appropriate acquisition devices, and CPU 4 would then store the received artifact information in the first study, and store the first study in storage unit 6. The first study would be given a first Study Instance UID, with the aforementioned artifact information being stored in a series within the first study, with the series being given a first Series Identifier and each artifact being given a first set of SOP Instance UIDs.

If after review of the study, a physician determines that an additional related examination is necessary, then a second study would be generated by a similar aforementioned process, with potentially a second Series Identifier UID and a second set of SOP Instance Identifiers. On the other hand, the second study may have previously been generated. Either way, an authorized user could view and identify study listings performed for the patient, at any one of the terminals 8, 10 or 14, for example, and command an automatic merging of the first and second studies. Herein, the term automatic corresponds to a automated computer implementation of the disclosed process after a user identification of the studies to be merged.

Terminal 10 could be a remote terminal connected to CPU 4 through a local LAN, and terminal 14 could be a remote terminal connected to CPU 12, which is connected to either CPU 4 or CPU 16 and Storage 6 via an Internet connection. Alternative modes of access of the patient's records would be available. Upon accessing the patients study records, an authorized user could command the above merging method. In addition, any of CPUs 4, 12 or 16 could utilize a computer readable medium including a program enabling the aforementioned merging commands.

Lastly, although only one source study has been indicated as being merged with a destination study, a multiple of studies may be merged with a single destination study, either at one time or at differing times, and composite studies may also be merged into a new composite study. Studies may even be merged when only one or none of the studies include artifacts such as images, patient measurements, findings, comments, waveforms, Doppler audio, or a medical study report, for example. Further, the present invention is not limited to the DICOM identifiers set forth above, but encompasses all merging of medical database records with similar attributes but with differing identifiers. Similarly, although the DICOM standard has been disclosed with the present invention being applied thereto, the present invention is not so limiting to exclude future standards for which the present invention would be also be applicable.

Thus, although a few preferred embodiments of the present invention have been shown and described, it would be appreciated by those skilled in the art that changes may be made in these embodiments without departing from the principles and spirit of the invention, the scope of which is defined in the claims and their embodiments.

What is claimed is:

1. A computer-implemented medical information merging method, comprising:
    identifying a patient's first collection of medical information with a first collection identifier, and a logically related or similar second collection of medical information with a second collection identifier, the first collection identifier being different from the second collection identifier;
    with a computer merging the patient's first collection of medical information with the second collection of medical information, to create a composite collection of medical information;
    during the merging, with the computer reconciling the first and second collection identifiers of the first and second collections of medical information;
    during said merging, with the computer automatically adding medical information, according to a protocol attribute, of the first or second collection of medical information into the other of the first or second collection of medical information in the creating of said composite collection of medical information; and
    at least one of displaying the composite collection of medical information on a display or storing the merged collection of medical information in a non-transitory computer memory.

2. The medical information merging method of claim 1, wherein the medical information is at least one of medical images, patient measurements, findings, comments, waveforms, Doppler audio, and a medical study report.

3. The medical information merging method of claim 2, further comprising computing patient measurement information of the first collection of medical information, based on the patient measurements in the second collection of medical information, upon said merging.

4. The medical information merging method of claim 1, wherein said adding comprises adding stage information of the second collection of medical information to the first collection of medical information according to a protocol attribute of the second collection of medical information.

5. The medical information merging method of claim 1, wherein the first and second collections of medical information include unique identifiers according to a lexicon of Digital Imaging and Communication in Medicine (DICOM).

6. The medical information merging method of claim 1, wherein said adding comprises adding a series instance identifier, for a series of the second collection of medical information, to the first collection of medical information without generating a new series instance identifier in the first collection of medical information for said series of the second collection of medical information.

7. The medical information merging method of claim 1, wherein said adding comprises adding new medical information of the second collection of medical information to the composite collection of medical information based on the new medical information including a collection identifier of the second collection of medical information.

8. The medical information merging method of claim 1, further comprising identifying the first and second collections of medical information, wherein said merging is initiated from a terminal remote from a storage unit containing either of the first and second collections of medical information.

9. The medical information merging method of claim 1, wherein the study identifiers of the first and second medical studies are unique among studies in a database having the distinct database entity.

10. A computer-implemented study merging method, comprising:
identifying a patient's first medical study, which first medical study includes a first study identifier, and a logically related or similar second medical study, which second medical study includes a second study identifier;
in response to a user request, with a computer merging the patient's first medical study with the second medical study to create a merged study, such that medically context-specific information stored in at least one of the first and second medical studies is merged based upon a protocol of at least one of the first and second studies, the protocol being indicated by an attribute of at least one of the first and second studies;
with the computer saving respective identifiers of the first and second studies;
with the computer deleting a distinct database identity for at least one of the first and second studies;
with the computer assigning a unique study identifier to the merged study; and
at least one of displaying the merged study on a terminal and storing the merged study in a non-transitory computer storage medium.

11. The study merging method of claim 10, wherein the medically context specific information is stage information.

12. The study merging method of claim 10, wherein the medically context specific information is measurement information.

13. A computer program product comprising a non-transitory computer readable medium in which is embodied a program having instructions executable by a computer to perform acts, said acts comprising:
identifying a patient's first collection of medical information with a first collection identifier, and a logically related or similar second collection of medical information with a second collection identifier;
merging the patient's first collection of medical information with the second collection of medical information, to create a composite collection of medical information;
wherein said merging includes reconciling the first and second collection identifiers of the first and second collections of medical information; and
wherein said merging includes automatically according to a protocol attribute, adding medical information, of the first or second collection of medical information into the other collection of medical information in the creating of said composite collection of medical information.

14. The computer program product of claim 13, wherein the medical information is at least one of medical images, patient measurements, findings, comments, waveforms, Doppler audio, and a medical study report.

15. The computer program product of claim 14, wherein said automatically adding comprises computing patient measurement information of the first collection of medical information, based on the patient measurements in the second collection of medical information, upon said merging.

16. The computer program product of claim 13, wherein said automatically adding comprises adding stage information of the second collection of medical information to the first collection of medical information according to a protocol attribute of the second collection of medical information.

17. The computer program product of claim 13, wherein the first and second collections of medical information include unique identifiers according to a lexicon of Digital Imaging and Communication in Medicine (DICOM).

18. The computer program product of claim 13, wherein said automatic adding comprises adding a series instance identifier, for a series of the second collection of medical information, to the first collection of medical information without generating a new series instance identifier in the first collection of medical information for said series of the second collection of medical information.

19. The computer program product of claim 13, wherein said automatic adding comprises adding new medical information of the first or second collections of medical information to the composite collection of medical information based on the new medical information including a collection of medical information identifier of either of the first or second collections of medical information.

20. The computer program product of claim 19, wherein said acts further comprise controlling the computer to notify a user when said adding of the new medical information is performed.

21. The computer program product of claim 13, further comprising controlling the computer to delete a distinct database identity of the second collection of medical information.

22. The computer program product of claim 13, wherein said acts further comprise controlling the computer to identify the first and second collections of medical information, wherein said merging is initiated from a terminal remote from a storage unit containing either of the first and second collections of medical information.

23. The computer program product of claim 13, wherein the study identifiers of the first and second medical studies are unique among studies in a database having the distinct database entity.

24. A computer program product comprising a non-transitory computer readable medium in which is embodied a program having instructions executable by a computer to perform acts, said acts comprising:
merging a patient's first medical study which includes a first study identifier with a logically related or similar second medical study which includes a second identifier to create a merged study, such that medically context-specific information stored in at least one of the first and second medical studies is merged based upon a protocol of at least one of the first and second studies, the protocol being indicated by an attribute of at least one of the first and second studies;
saving respective identifiers of the first and second studies;
deleting at least one of the first and second study identifiers; and assigning a unique study identifier to the merged study.

25. The computer program product of claim 24, wherein the medically context-specific information is stage information.

26. The computer program product of claim 24, wherein the medically context-specific information is measurement information.

27. A computer-implemented medical study merging method, comprising:
identifying, in accordance with a lexicon of Digital Imaging and Communication in Medicine (DICOM), a patient's related first and second medical studies to be merged, the first medical study having a first identifier and the second medical study having a second identifier different from the first medical study identifier;
with one or more processors, merging the first medical study with the second medical study, according to a protocol attribute, to create a resultant composite study having a study identifier different from at least one of the first and second identifiers of the first and second medical studies, wherein, in accordance with said lexicon, the merging includes an automatic, processor-implemented adding of a series of the second medical study to the composite study, the series of the second medical study having a series identifier identical to a pre-merge corresponding series identifier, with the series of the second medical study including at least an artifact with an artifact identifier identical to a pre-merge corresponding artifact identifier, such that the composite study includes series and corresponding series identifiers from both the premerged first and second medical studies; and at least one of generating a human viewable display on a display device of the composite study and storing the composite study in a non-transitory computer storage device.

28. The medical study merging method of claim 27, wherein the composite study is assigned a unique study identifier of the first medical study.

* * * * *